US009398939B2

(12) United States Patent
Morehead

(10) Patent No.: US 9,398,939 B2
(45) Date of Patent: Jul. 26, 2016

(54) DYNAMIC DENTAL CROWN

(76) Inventor: Gordon Ray Morehead, Colorado Springs, CO (US)

( * ) Notice: Subject to any disclaimer, the term of this patent is extended or adjusted under 35 U.S.C. 154(b) by 0 days.

(21) Appl. No.: 13/229,067

(22) Filed: Sep. 9, 2011

(65) Prior Publication Data

US 2013/0065199 A1    Mar. 14, 2013

(51) Int. Cl.
*A61C 13/10* (2006.01)
*A61C 8/00* (2006.01)
*A61C 13/265* (2006.01)

(52) U.S. Cl.
CPC .............. *A61C 13/10* (2013.01); *A61C 8/0086* (2013.01); *A61C 13/2656* (2013.01)

(58) Field of Classification Search
CPC ... A61C 13/10; A61C 13/2656; A61C 8/0086
USPC ................. 433/191–196, 167–170, 172–174, 433/177–178, 218–221, 202.1–212.1
See application file for complete search history.

(56) References Cited

U.S. PATENT DOCUMENTS

| | | | | |
|---|---|---|---|---|
| 4,518,357 A | * | 5/1985 | Brinkmann et al. | 433/173 |
| 4,993,950 A | * | 2/1991 | Mensor, Jr. | 433/173 |
| 5,221,206 A | * | 6/1993 | Nardi | A61C 13/2656 433/181 |
| 5,678,994 A | * | 10/1997 | Morehead | A61C 13/1026 433/169 |
| 5,871,357 A | * | 2/1999 | Tseng | 433/189 |
| 6,019,604 A | * | 2/2000 | Gougeon | A61C 8/0086 433/168.1 |
| 7,704,076 B2 | * | 4/2010 | Mullaly et al. | 433/174 |
| 2002/0177103 A1 | * | 11/2002 | Pelak | A61C 8/0048 433/173 |
| 2010/0159420 A1 | * | 6/2010 | Mullaly et al. | 433/174 |
| 2012/0034578 A1 | * | 2/2012 | Bulard et al. | 433/174 |
| 2012/0045737 A1 | * | 2/2012 | Ang | 433/177 |

* cited by examiner

*Primary Examiner* — Cris L Rodriguez
*Assistant Examiner* — Mirayda A Aponte
(74) *Attorney, Agent, or Firm* — Jacque R. Wilson; Carson Boxberger LLP

(57) ABSTRACT

An artificial tooth system, including a denture-engaging body portion, a first recess formed in the denture-engaging body portion, and a pivot base positioned within the first recess and operationally connected to the denture-engaging body portion. A generally spherical ball connector extends from the pivot base. A pivot platform is pivotably connected to the generally spherical ball portion and a resilient ring is positioned around the generally spherical ball connector and situated between the pivot base and the pivot platform. A membrane is sealingly connected around the pivot base and the pivot platform. The tooth also includes a crown portion with a second recess formed in the crown portion, wherein the pivot platform is positioned within the second recess.

1 Claim, 3 Drawing Sheets

DYNAMIC DENTAL CROWN

TECHNICAL FIELD

The novel technology relates generally to the field of dentistry, and, more particularly, to an artificial tooth having a dynamic crown portion.

BACKGROUND

A natural tooth flexes by moving within the periodontal tissue surrounding the root such that the tooth's effective flexural center is relatively low, which is important in biting, chewing and mastication. In contrast, artificial teeth are rigid, and denture wearers often experience discomfort when biting and chewing food. In particular, denture wearers are prone to soreness in their lower gums because they have to apply excess pressure when they chew. The excess pressure is required because since the dentures are rigid, with the teeth rigidly attached thereto, it s difficult for the wearer to feel small jaw movements, in particular side-to-side and forward-to-backward movement of the upper and lower jaws against each other, that are basic to chewing. Without this sensory feedback, the denture wearer has to apply excess pressure to accomplish chewing. This excess pressure and associated friction, is transmitted directly through the rigid dentures and into the wearer's gums, making them tender and sore. Accordingly, it is desirable to have an artificial tooth that mimics the flexion of a natural tooth. Thus, there is a need for an artificial tooth that can automatically flex like a natural tooth during mastication. The present novel technology arises from an attempt to address this need.

SUMMARY

The present novel technology relates to an artificial tooth having built in flexibility. One object of the present novel technology is to provide an improved artificial tooth. Related objects and advantages of the present novel technology will be apparent from the following description.

DESCRIPTION OF THE PREFERRED EMBODIMENTS

Figure 1:
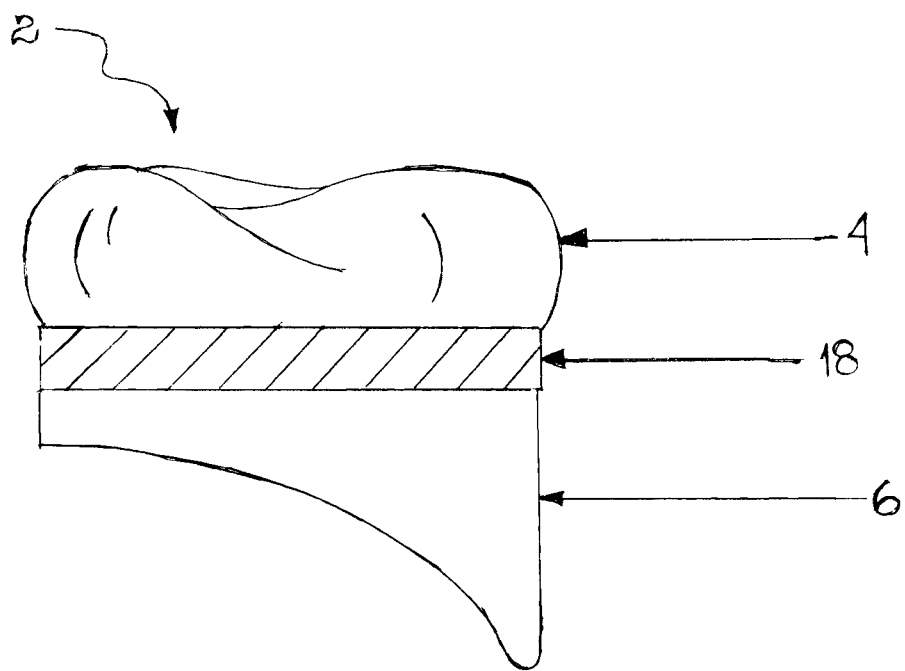
FIG. 1 is a side view of an artificial tooth according to one embodiment of the present novel technology.
Figure 2:
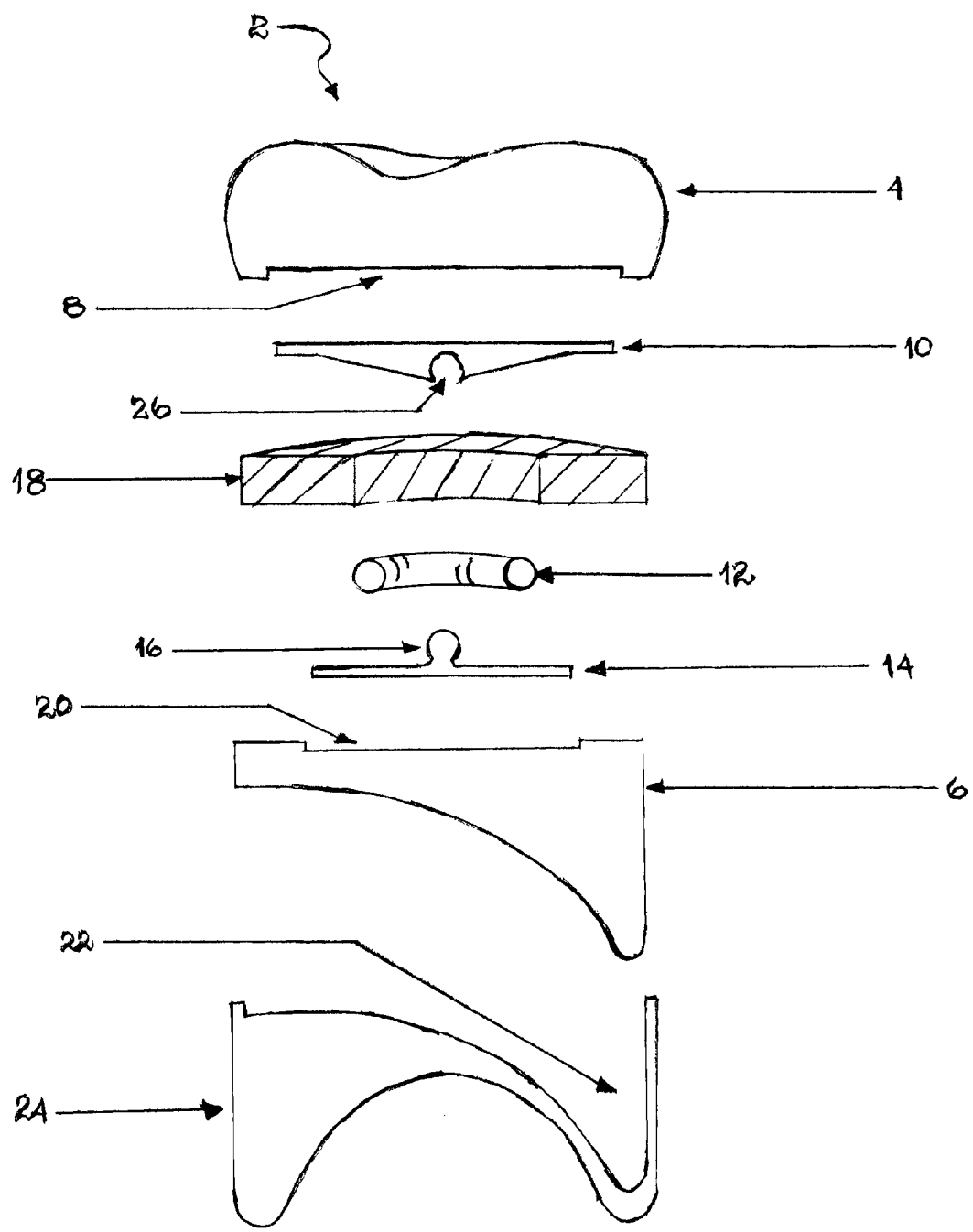
FIG. 2 is an exploded cross-sectional view of the tooth of FIG. 1.
Figure 3:
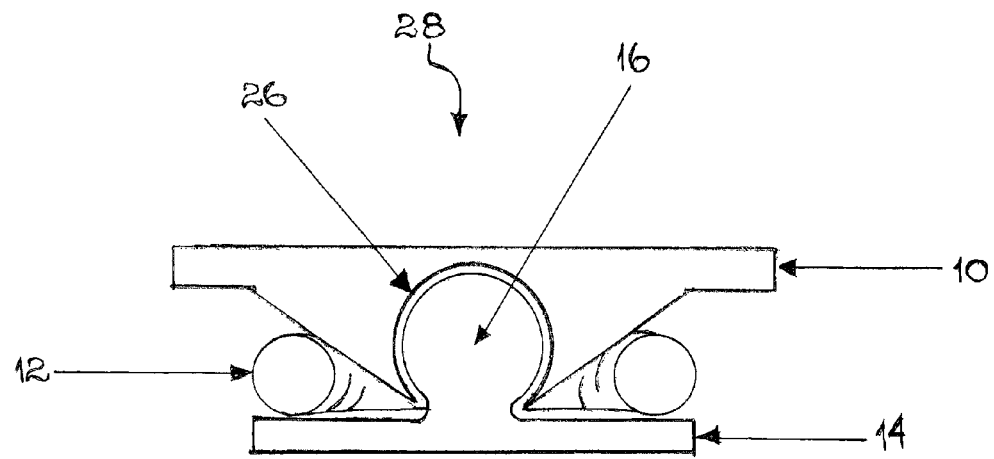
FIG. 3 is an exploded cross-sectional view of the pivot assembly of FIG. 2.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

FIGS. 1-4 illustrate one embodiment of the present novel technology, an artificial tooth 2 having a crown portion 4, a membrane portion 18 and a denture-engaging or body portion 6. The crown portion 4 defines the working surface of the tooth 2 that directly engages food during chewing. The denture-engaging portion 6 in part mimics the function of a natural tooth's root. The membrane 18 is typically a generally fluid-impervious seal, and is more typically sealingly connected between the crown portion 4 and the denture-engaging portion 6 to define an integral tooth 2.

The crown portion 4 is typically connected to a female connector 10, and more typically the crown portion 4 includes a recess 8 formed therein for receivably connecting with the female connector 10, although the crown portion 4 may remain unrecessed and connected to the female connector 10, such as through a generally planar crown connection interface. Likewise, the body portion 6 is connected to a male connector 14, and more typically includes a recess 20 for receivably connecting to the male connector 14. Of course, the crown portion 4 may be connected to the male connector 14 and the body portion 6 may be connected to the female connector 10.

The crown portion 4 is pivotably connected to the body portion 6 through the pivot assembly 28. The pivot assembly is typically a ball-and-socket connector, wherein the ball 16 of the male connector 14 is matable with the socket 26 of the female connector 10. The pivot assembly 28 provides vertical integrity to the tooth 2. The pivot assembly 28 may optionally include an O-ring 12 disposed between the female connector 10 and the male connector 14.

The male and female connectors 14, 10 are preferably made of medical grade steel, ceramic composite material, or the like. The male and female connectors 14, 10 are typically precision machined such that the male connector 14 may be mated readily and securely with the female connector 10, to promote a generally frictionless, yet snug, connection so as to impart vertical integrity to the tooth 2. The male and female connectors 14, 10 are mated by snapping the male ball 16 into the female socket 26. The ball 16 typically defines a diameter slightly greater than the opening of the socket 26. The O-ring 12 is typically positioned around the ball 16 before the ball 16 is snapped into the socket 26.

The O-ring 12 operates to both assist in the assembly of the pivot assembly 28, and thus the tooth 2, by maintaining the female connector 10 in static relation to the male connector 14 during incorporation of the membrane 18. The O-ring 12 likewise assists with the support of the mated male connector 14 and the female connector 10, as well as to help maintain the connectors 10, 14 in an uncompressed static relationship with each other 10, 14. In other words, the O-ring 12 both supports the crown portion 4 when not engaged in chewing, and also dampens the motion of the crown portion 4 while chewing.

Figure 4:
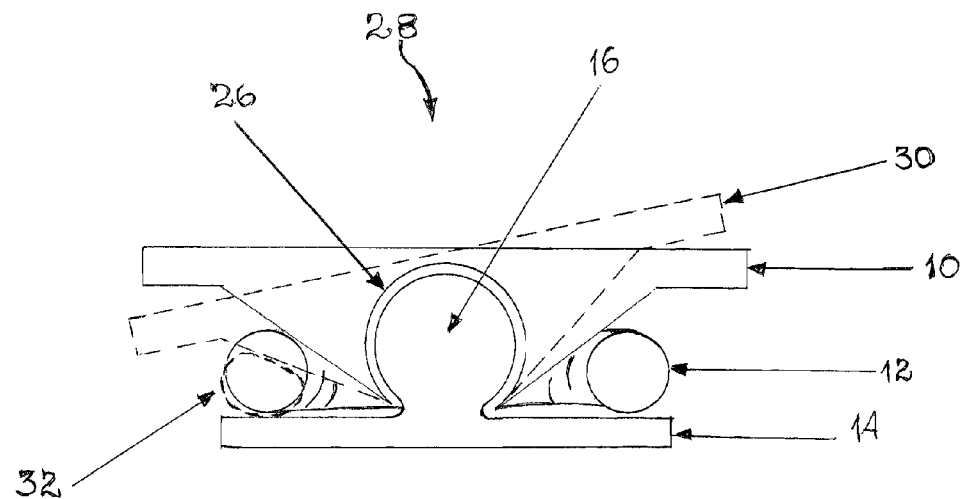
FIG. 4 is an enlarged cross sectional view of the pivot assembly of FIG. 3.

During mastication of a food bolus, the socket 26 pivots about the ball 16, providing a deflective force to the food bolus. The application of the deflective force both aids in chewing and protects the gums from the transmission of excess forces through the tooth 2. The O-ring 12 operates to limit the angel of deflection of the crown portion 4 during mastication. When the female connector 10 has been deflected to a position define a deflected connector 30 (as seen in FIG. 4), the O-ring 12 undergoes compression to define a partially compressed O-ring 32 to mitigate deflection of the crown portion 4 and dampen the deflection forces. Upon release of the mastication forces, the O-ring 12 returns to its uncompressed dimensions, exerting a counter force on the pivot assembly 28 and thus the crown portion 4.

The O-ring 12 is typically made of medical grade silicone or rubber. The O-ring typically has an outside diameter of between about 1 millimeter and about 6 millimeters, and a side diameter of between about 0.5 millimeters and about 5 millimeters, with a cross-section of between about 0.25 millimeters and about 1 millimeter.

The tooth 2 allows slight movement when subjected to typical mastication forces, whereby the crown portion 4 articulates independently of the body portion 6, mimicking the movement of a natural tooth and reducing the pressure transmitted to the gums through the tooth 2. The deflection of the crown portion thus both mitigates soreness of the gums and assists in chewing food, much in the same manner of a natural tooth.

The crown 4 is typically prepared by forming a recess 8 therein to receive the female connector 10. Likewise, the body 6 is prepared by forming a recess 20 therein to receive the male connector 14. The female connector 10 is placed within the recess 8 and secured therein by any convenient means, such as with dental cement or the like. The male connector is likewise placed in the recess 20 and similarly secured therein. Alternately, the crown and body portions 4, 6 may be connected to the respective connectors 10, 14 by any convenient means without the necessity of a recess 8, 20.

The female connector 10 is typically of a diameter from about 3 millimeters to about 9 millimeters. The male connector 14 is typically of a diameter similar to, or slightly less than, the female connector 10, more typically from about 1 millimeter to about 7 millimeters.

The tooth 2, with the crown and body portions matedly connected through the pivot assembly 28, is typically sealed with the annular membrane 18. The membrane 18 is typically positioned to surround and enclose the pivot assembly 28 and acts to seal the crown and body portions 4, 6 together to define the tooth 2. The membrane 18 simulates the mechanical properties of a periodontal ligament extending between a natural tooth and a natural gum.

The membrane 18 may be formed from any suitable material, typically selected from materials approved for use in dental devices. The membrane 18 is typically puncture resistant, resistant or impervious to fluids and foodstuffs, and erosion resistant. The membrane 18 typically has an outside diameter from about ½ a millimeter to about 6 millimeters, and a cross sectional thickness from about 1 millimeter to about 2 millimeters.

The membrane 18 typically surrounds the pivot assembly 28 and forms a seal between the crown portion 4 and the body portion 6. The membrane 18 generally prevents penetration of fluids and foodstuffs from the oral cavity and surrounding environment from penetrating the tooth 2. Further, the membrane 18 is typically resilient and may fluctuate between a normal resting state and a compressed state when mastication forces are applied. During a mastication event, the membrane 18 may also serve to limit the angle of deflection of the pivot assembly 28/crown portion 4 relative to the body portion 6. Upon relaxation of the mastication forces, the membrane 18 returns to its uncompressed, relaxed state and the pivot assembly 28/crown portion 4 then is urged back towards its no normal resting state.

In operation, tooth 2 is inserted and secured into a denture recess 22 formed in a denture base 24, typically by means of common dental construction procedures. The denture base 24 may then be inserted into the oral cavity and held in place by any convenient denture adhesive. During chewing, the pivot assembly 28 allows the crown portion 4 to deflect about a (typically vertical) axis and thus aids the user in mastication of a food bolus by adding frictional and planar shearing forces to the crushing forces generated by the jaws, more closely mimicking mastication with a natural tooth. The O-ring 12 and the membrane 18 both assist in the return of the pivot assembly 28 (and thus the crown portion 4) to its normal resting orientation when no mastication forces are applied to urge the crown portion away therefrom.

Generally, the pivot assembly 28 provides a higher flexion point within the tooth 2. The higher flexion point enables the user to provide less chewing pressure to achieve deflection of the crown portion 4 to mimic the behavior of a natural tooth.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. An artificial tooth system for attachment to a denture, said artificial tooth system comprising:
 a crown, said crown having a generally flat bottom surface;
 a female connector, said female connector having a generally flat top surface, a conical bottom surface, and a spherical socket centrally disposed within said conical bottom surface, said flat top surface of said female connector fixedly attached to said bottom surface of said crown;
 a male connector, said male connector having a generally flat bottom surface and an opposing top surface, said top surface of said male connector having a spherical protruding ball, said ball of said male connector pivotally and rotationally inserted into said socket of said female connector thereby forming a ball and socket joint;
 a denture engaging portion, the top of said denture engaging portion fixedly attached to the bottom of said male connector;
 a flexible o-ring, said flexible o-ring disposed around said ball and between said male connector and said female connector; and
 a flexible cylindrical membrane, said membrane disposed around said o-ring and between said male connector and said female connector,
 wherein said crown movable relative to said denture engaging portion.

* * * * *